United States Patent
Jeong et al.

(10) Patent No.: US 11,583,512 B2
(45) Date of Patent: Feb. 21, 2023

(54) COMPOSITION FOR RELIEVING ITCH OR IRRITATION OF SKIN, COMPRISING THYMOL TRIMETHOXYCINNAMATE

(71) Applicant: Amorepacific Corporation, Seoul (KR)

(72) Inventors: Yeonsu Jeong, Yongin-si (KR); Bongsoo Pi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 84 days.

(21) Appl. No.: 17/388,581

(22) Filed: Jul. 29, 2021

(65) Prior Publication Data

US 2022/0031648 A1  Feb. 3, 2022

(30) Foreign Application Priority Data

Aug. 3, 2020 (KR) .................. 10-2020-0096647

(51) Int. Cl.
 *A61K 31/216* (2006.01)
 *A61P 17/04* (2006.01)
 *A61K 8/37* (2006.01)

(52) U.S. Cl.
 CPC .............. *A61K 31/216* (2013.01); *A61K 8/37* (2013.01); *A61P 17/04* (2018.01)

(58) Field of Classification Search
 CPC .......... A61K 31/216; A61K 8/37; A61P 17/04
 See application file for complete search history.

(56) References Cited

U.S. PATENT DOCUMENTS

| | | |
|---|---|---|
| 2010/0278760 A1 | 11/2010 | Kouzuki et al. |
| 2015/0353469 A1 | 12/2015 | Le Roy et al. |

FOREIGN PATENT DOCUMENTS

| | | |
|---|---|---|
| JP | 2012-530114 A | 11/2012 |
| KR | 2002-0081225 A | 10/2002 |
| KR | 10-0457949 B1 | 11/2004 |
| KR | 10-2018-0017459 A | 2/2018 |
| KR | 10-2018-0045728 A | 5/2018 |
| WO | 02/44120 A1 | 6/2002 |
| WO | 2010/146142 A9 | 12/2010 |

OTHER PUBLICATIONS

John Hwan Lee et al., "Antimelanogenic Efficacy of Melasolv (3,4,5-Trimethoxycinnamate Thymol Ester) in Melanocytes and Three-Dimensional Human Skin Equivalent", Skin Pharmacol Physiol; Jun. 30, 2017, pp. 190-196, vol. 30.

Jun-Ho Lee, "A Monoclonal Antibody that Targets a Nav1-7 Channel Voltage Sensor for Pain and Itch Relief", Cell, Jun. 5, 2014, pp. 1393-1404, vol. 157.

Grazia Devigili et al., "Paroxysmal itch caused by gain-of-function Nav1.7 mutation", PAIN, 2014, pp. 1702-1707, vol. 155.

*Primary Examiner* — Jeffrey S Lundgren
*Assistant Examiner* — William Y Lee
(74) *Attorney, Agent, or Firm* — Sughrue Mion, PLLC

(57) ABSTRACT

The present disclosure discloses a composition for relieving skin itch or irritation, which contains thymol trimethoxycinnamate or a stereoisomer, salt, hydrate or solvate thereof as an active ingredient, and a method for relieving skin itch or skin irritation by administering the composition to a subject in need of reliving of skin itch or irritation. The composition according to an aspect of the present disclosure has a superior effect of relieving skin itch or skin irritation by inhibiting the voltage-gated sodium channel Nav1.7 without side effects.

10 Claims, 2 Drawing Sheets

[FIG. 1]
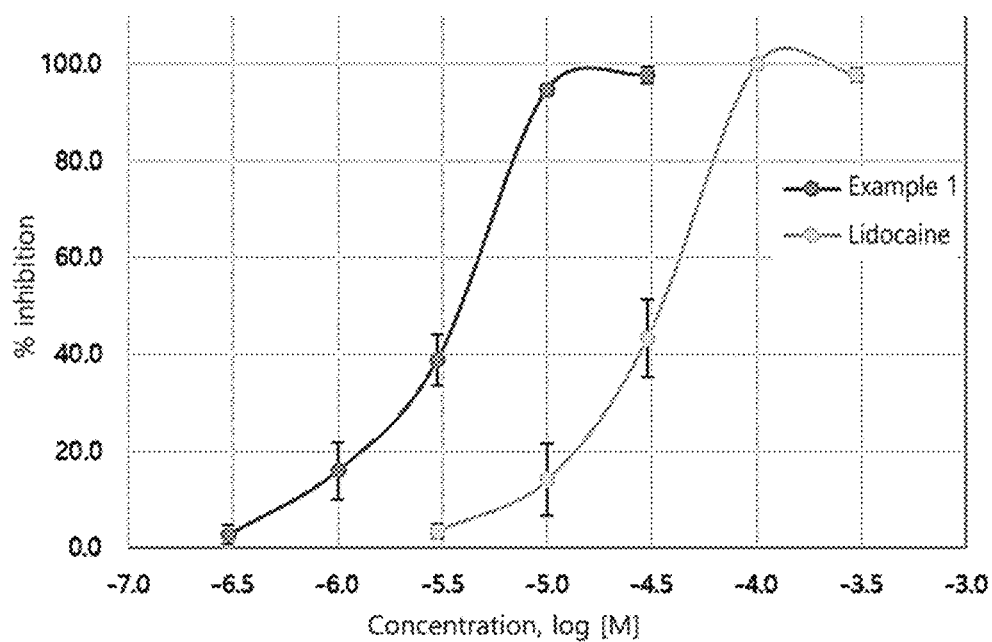

[FIG. 2]
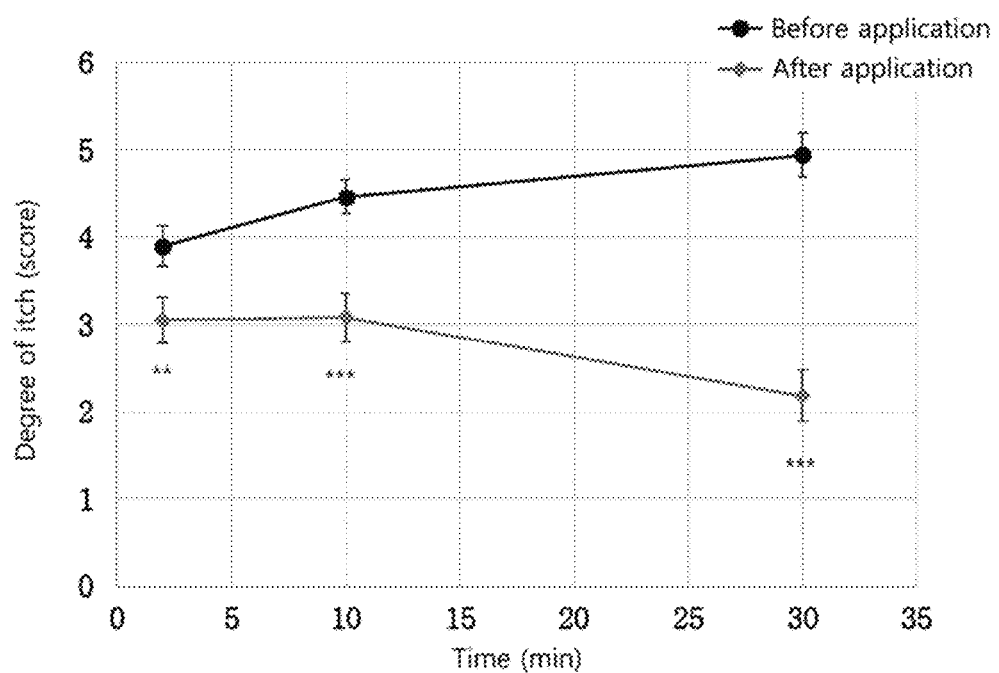

COMPOSITION FOR RELIEVING ITCH OR IRRITATION OF SKIN, COMPRISING THYMOL TRIMETHOXYCINNAMATE

CROSS-REFERENCE TO RELATED APPLICATION

This application claims the priority of Korean Patent Application No. 10-2020-0096647 filed on Aug. 3, 2020, the contents of which in their entirety are herein incorporated by reference.

TECHNICAL FIELD

The present disclosure relates to a composition for relieving skin itch or irritation.

BACKGROUND ART

Itch is a sensation that causes the desire to scratch as a main symptom of a skin disease. It is an avoidance response to harmful stimulation and may be induced not only by a skin disease but also by a systemic disease or a mental disease.

Mediators of both the central and peripheral nervous systems play an important role in pruritus (itch). Proinflammatory mediators cause pruritus in inflammatory skin diseases such as hives. Most of these mediators may cause other symptoms of inflammation, i.e., pain, vasodilation-induced erythema, increased vascular permeability, etc. In addition, itch may be caused by increased activity of histamines, other factors secreted by mast cells, prostaglandins, etc. Besides, itch signals may also be transmitted by the receptors distributed in peripheral nerves by such compounds as bile acid, proteases, cytokines, neuropeptides, chloroquine and opioids. Although various anti-itch drugs are used for these targets, they have limitations. Calamine lotion has a weak effect of relieving itch and steroids are not suitable for long-term use although they relieve itch by reducing inflammation. Calcineurin inhibitors are known to induce pain temporarily and increase the risk of malignant tumor. While menthol and capsaicin lotion can relieve itch by activating ion channels (TRPM8, TRPV1, etc.) through neurons, they are quite irritant. Antihistamines are limited in that they are restricted to histamine-induced pruritus such as hives.

Meanwhile, local anesthetics such as lidocaine, pramoxine and prilocaine, which prevent irritation and itch signal transduction by reducing the transport of sodium ions through the neural network, are used to relieve itch and pain.

Various receptors for mediators inducing irritation, pain and itch are distributed in the peripheral tissues of skin and cutaneous nerves. The stimulations received by these receptors are delivered to the central nervous system in the form of electrical signals. Voltage-gated sodium channels are known as major ion channels that play such a role. The relationship between the voltage-gated sodium channels and itch has been reported recently. The local anesthetics lidocaine, pramoxine, etc., which are used as itch-relieving agents, are traditional nonselective sodium channel blockers.

DISCLOSURE

Technical Problem

In an aspect, the present disclosure is directed to providing a composition having a superior effect of relieving skin itch or skin irritation and a method for relieving skin itch or skin irritation.

Technical Solution

In an aspect, the present disclosure provides a method for relieving skin itch or skin irritation, which includes administering an effective amount of a composition containing thymol trimethoxycinnamate or a stereoisomer, salt, hydrate or solvate thereof to a subject in need of relieving skin itch or skin irritation.

In an exemplary embodiment, the thymol trimethoxycinnamate may be represented by Chemical Formula 1.

[Chemical Formula 1]

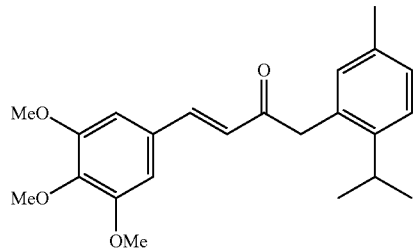

In an exemplary embodiment, an administration dosage of the thymol trimethoxycinnamate or a stereoisomer, salt, hydrate or solvate thereof may be 0.37-37 mg/kg/day.

In an exemplary embodiment, the composition may inhibit the voltage-gated sodium channel Nav1.7.

In an exemplary embodiment, the skin itch or skin irritation may be induced by a chemical substance.

In an exemplary embodiment, the chemical substance may be a veratrum alkaloid, and the veratrum alkaloid may be veratridine.

In an exemplary embodiment, the composition may be a composition for external application to skin.

In an exemplary embodiment, the composition may be a food, cosmetic or pharmaceutical composition.

Advantageous Effects

In an aspect, a composition containing thymol trimethoxycinnamate or a stereoisomer, salt, hydrate or solvate thereof according to the present disclosure exhibits excellent skin itch-relieving effect without side effects.

In another aspect, a composition containing thymol trimethoxycinnamate or a stereoisomer, salt, hydrate or solvate thereof according to the present disclosure exhibits excellent skin irritation-relieving effect without side effects.

In another aspect, a composition containing thymol trimethoxycinnamate or a stereoisomer, salt, hydrate or solvate thereof according to the present disclosure can inhibit the voltage-gated sodium channel Nav1.7.

BRIEF DESCRIPTION OF DRAWINGS

FIG. 1 shows the inhibition rate of the voltage-gated sodium channel Nav1.7 depending on treatment with thymol trimethoxycinnamate.

FIG. 2 shows itch-relieving effect depending on treatment with thymol trimethoxycinnamate (paired t-test p<0.01, * p<0.001).

BEST MODE

Hereinafter, the present disclosure is described in detail.

In an aspect, the present disclosure provides a method for relieving skin itch or skin irritation, which includes administering an effective amount of a composition containing thymol trimethoxycinnamate or a stereoisomer, salt, hydrate or solvate thereof to a subject in need of relieving skin itch or skin irritation.

In an aspect, the present disclosure provides a composition for relieving skin itch or irritation, which contains thymol trimethoxycinnamate or a stereoisomer, salt, hydrate or solvate thereof.

In an exemplary embodiment, the thymol trimethoxycinnamate is 5-methyl-2-propan-2-ylphenyl (E)-3-(3,4,5-trimethoxyphenyl)prop-2-enoate that may be represented by Chemical Formula 1.

[Chemical Formula 1]

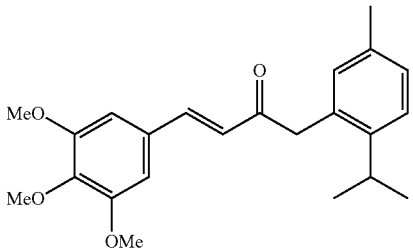

In the present disclosure, the "stereoisomer" includes optical isomers, e.g., essentially pure enantiomers, essentially pure diastereomers or mixtures thereof.

In the present disclosure, "essentially pure" means that a specific compound having enantiomers or diastereomers is present at about 90% (w/w) or more, specifically about 95% or more, more specifically about 97% or more or about 98% or more, further more specifically about 99% or more, even more specifically about 99.5% or more when used in connection with the enantiomers or diastereomers.

In the present disclosure, the "salt" refers to a salt according to an aspect of the present disclosure which is acceptable in medications, cosmetics and foods and has the desired activity of the parent compound. The salt may include (1) an acid addition salt formed from an inorganic acid such as hydrochloric acid, hydrobromic acid, sulfuric acid, nitric acid, phosphoric acid, etc. or an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicylco[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is substituted. In addition, the salt may be a pharmaceutically acceptable salt.

In the present disclosure, "pharmaceutically acceptable" means that use of a general medicinal dosage avoids a significant toxic effect and thus can be accepted or is accepted as appropriate for application to animals, particularly to human, by the government or a corresponding regulatory organization, or is listed in the pharmacopeia or regarded as being listed in general pharmacopeias.

In the present disclosure, the "hydrate" means a compound bonded to water and is used in a broad concept, including an inclusion compound in which water and the compound have no chemical bonding therebetween.

In the present disclosure, the "solvate" means a higher-order compound formed between a molecule or ion of a solute and a molecule or ion of a solvent.

In the present disclosure, the "active ingredient" means an ingredient which exhibits a desired activity either alone or the presence of a carrier which lacks activity.

In an exemplary embodiment, a content of the thymol trimethoxycinnamate or a stereoisomer, salt, hydrate or solvate thereof may be 0.001-20 wt % based on the total weight of the composition. If the content of the thymol trimethoxycinnamate or a stereoisomer, salt, hydrate or solvate thereof is less than 0.001 wt %, the effect of relieving skin itch or irritation is decreased. And, if the content exceeds 20 wt %, formulation stability is decreased. Specifically, the content of the thymol trimethoxycinnamate or a stereoisomer, salt, hydrate or solvate thereof may be 0.001 wt % or more, 0.002 wt % or more, 0.003 wt % or more, 0.004 wt % or more, 0.005 wt % or more, 0.01 wt % or more, 0.02 wt % or more, 0.03 wt % or more, 0.04 wt % or more, 0.05 wt % or more, 0.06 wt % or more, 0.07 wt % or more, 0.1 wt % or more, 0.2 wt % or more, 0.3 wt % or more, 0.4 wt % or more, 0.5 wt % or more, 0.6 wt % or more, 0.7 wt % or more, 1 wt % or more, 1.5 wt % or more, 2 wt % or more, 2.5 wt % or more, 3 wt % or more, 3.5 wt % or more, 4 wt % or more, 4.5 wt % or more or 5 wt % or more, and 20 wt % or less, 19.9 wt % or less, 19.8 wt % or less, 19.7 wt % or less, 19.6 wt % or less, 19.5 wt % or less, 19.4 wt % or less, 19.3 wt % or less, 19.2 wt % or less, 19.1 wt % or less, 19 wt % or less, 18.8 wt % or less, 18.6 wt % or less, 18.4 wt % or less, 18.2 wt % or less, 18 wt % or less, 17.8 wt % or less, 17.6 wt % or less, 17.4 wt % or less, 17.2 wt % or less, 17 wt % or less, 16.8 wt % or less, 16.6 wt % or less, 16.4 wt % or less, 16.2 wt % or less, 16 wt % or less, 15.5 wt % or less, 15 wt % or less, 14.5 wt % or less, 14 wt % or less, 13.5 wt % or less, 13 wt % or less, 12.5 wt % or less, 12 wt % or less, 11.5 wt % or less, 11 wt % or less, 10.5 wt % or less or 10 wt % or less.

In an exemplary embodiment, the thymol trimethoxycinnamate or a stereoisomer, salt, hydrate or solvate thereof may be administered with an administration dosage of 0.37-37 mg/kg/day. If the administration dosage of the thymol trimethoxycinnamate or a stereoisomer, salt, hydrate or solvate thereof is less than 0.37 mg/kg/day, the effect of relieving skin itch or irritation may be decreased. And, if the administration dosage exceeds 37 mg/kg/day, skin irritation may occur. Specifically, the administration dosage of the thymol trimethoxycinnamate or a stereoisomer, salt, hydrate or solvate thereof may be 0.37 mg/kg/day or more, 0.38 mg/kg/day or more, 0.39 mg/kg/day or more, 0.4 mg/kg/day or more, 0.41 mg/kg/day or more, 0.42 mg/kg/day or more, 0.43 mg/kg/day or more, 0.44 mg/kg/day or more, 0.45 mg/kg/day or more, 0.5 mg/kg/day or more, 0.55 mg/kg/day or more, 0.6 mg/kg/day or more, 0.65 mg/kg/day or more, 0.7 mg/kg/day or more, 0.8 mg/kg/day or more, 0.9 mg/kg/ day or more, 1 mg/kg/day or more, 1.1 mg/kg/day or more, 1.2 mg/kg/day or more, 1.3 mg/kg/day or more, 1.5 mg/kg/day or more, 1.7 mg/kg/day or more, 2 mg/kg/day or more, 3 mg/kg/day or more, 4 mg/kg/day or more, 5 mg/kg/day or more, 6 mg/kg/day or more, 7 mg/kg/day or more, 8 mg/kg/day or more, 9 mg/kg/day or more, 10 mg/kg/day or more, 11 mg/kg/day or more, 12 mg/kg/day or more, 13 mg/kg/day or more, 14 mg/kg/day or more or 15 mg/kg/day or more, and 37 mg/kg/day or less, 36.5 mg/kg/day or less, 36 mg/kg/day or less, 35.5 mg/kg/day or less, 35 mg/kg/day or less, 34.5 mg/kg/day or less, 34 mg/kg/day or less, 33.5 mg/kg/day or less, 33 mg/kg/day or less, 32.5 mg/kg/day or less, 32 mg/kg/day or less, 31.5 mg/kg/day or less, 31 mg/kg/day or less, 30.5 mg/kg/day or less, 30 mg/kg/day or less, 29.5 mg/kg/day or less, 29 mg/kg/day or less, 28.5 mg/kg/day or less, 28 mg/kg/day or less, 27.5 mg/kg/day or less, 27 mg/kg/day or less, 26.5 mg/kg/day or less, 26 mg/kg/day or less, 25.5 mg/kg/day or less, 25 mg/kg/day or less, 24.5 mg/kg/day or less, 24 mg/kg/day or less, 23.5 mg/kg/day or less or 23 mg/kg/day or less.

In an exemplary embodiment, the composition may inhibit the voltage-gated sodium channel Nav1.7.

In an exemplary embodiment, the skin itch or skin irritation may be induced by a chemical substance. For example, the chemical substance may be a veratrum alkaloid, and the veratrum alkaloid may be specifically veratridine.

In an exemplary embodiment, the composition may be administered transdermally or externally to skin, although not being limited thereto.

In an exemplary embodiment, the composition may be a cosmetic composition. The cosmetic composition may be formulated, for example, into a softening lotion, an astringent lotion, a nourishing lotion, a nourishing cream, a massage cream, an eye cream, an eye essence, essence, a cleansing cream, a cleansing lotion, a cleansing foam, a cleansing water, a pack, a powder, a body lotion, a body cream, a body essence, a body cleanser, a hair dye, a shampoo, a rinse, a hair fixative, a hair tonic, an ointment, a gel, a cream, a patch, a spray, a powder, a skin adhesive, etc., although not being limited thereto.

In addition, each formulation may contain, in addition to the essential ingredient described above, other ingredients that may be selected by those skilled in the art without difficulty depending on the type of the formulation, purpose of use, etc.

The cosmetic composition may be provided as any topically applicable formulation. For example, it may be provided as a solution, an emulsion obtained by dispersing an oil phase in an aqueous phase, a suspension, a solid, a gel, a powder, a paste, a microneedle, a foam or an aerosol. These formulations may be prepared according to common methods in the art.

The cosmetic composition according to the present disclosure may further contain functional additives and ingredients contained in general cosmetic compositions in addition to the compound of the present disclosure. The functional additive may include an ingredient selected from a group consisting of a water-soluble vitamin, an oil-soluble vitamin, a polypeptide, a polysaccharide, a sphingolipid and a seaweed extract. The cosmetic composition according to the present disclosure may further contain another ingredient that can provide synergistic effect to the main effect within a range not negatively affecting the main effect. In addition, the cosmetic composition according to the present disclosure may further contain a wetting agent, an emollient, a surfactant, a UV absorbent, an antiseptic, a sterilizer, an antioxidant, a pH control agent, an organic or inorganic pigment, a flavor, a cooling agent or an antiperspirant. The mixing amount of the ingredient may be easily determined by those skilled in the art within a range not negatively affecting the purpose and effect of the present disclosure. The mixing amount may be 0.001-10 wt %, specifically 0.01-3 wt %, based on the total weight of the composition.

In an exemplary embodiment, the composition may be a food composition. The food composition may be formulated into, for example, a tablet, a granule, a pill, a powder, a liquid such as a drink, a caramel, a gel, a bar, a tea bag, etc., although not being specially limited thereto. Each formulation may contain ingredients commonly used in the art that may be selected by those skilled in the art without difficulty depending on the type of the formulation, purpose of use, etc. in addition to the active ingredient. A synergistic effect may be achieved with the active ingredient is used together with other ingredients.

In an exemplary embodiment, the food composition may contain various nutrients, vitamins, minerals (electrolytes), flavorants such as synthetic flavorants or natural flavorants, colorants, extenders (cheese, chocolate, etc.), pectic acid and its salts, alginic acid and its salts, organic acids, protective colloidal thickeners, pH control agents, stabilizer, antiseptic, glycerin, alcohols, carbonating agents used in carbonated beverages, etc. In addition, the food composition according to an exemplary embodiment may further contain a pulp for preparation of a natural fruit juice, a fruit juice beverage or a vegetable beverage. These ingredients may be used either alone or in combination. The content of these additives is of no great importance. In general, they are contained within a range of about 0-50 parts by weight based on 100 parts by weight of the composition according to an exemplary embodiment.

In an exemplary embodiment, the composition may be a pharmaceutical composition. The pharmaceutical composition may be administered orally, parenterally, rectally, topically, transdermally, intravenously, intramuscularly, intraperitoneally, subcutaneously, etc. Formulations for oral administration may include a tablet, a pill, a soft or hard capsule, a granule, a powder, a fine granule, a liquid, an emulsion or a pellet, although not being limited thereto. Formulations for parenteral administration may include a solution, a suspension, an emulsion, a gel, an injection, a medicinal drip, a suppository, a patch or a spray, although not being limited thereto. The formulations may be prepared easily by common methods in the art and may further contain a surfactant, an excipient, a wetting agent, an emulsification accelerator, a suspending agent, a salt or a buffer for control of osmotic pressure, a colorant, a flavor, a stabilizer, an antiseptic, a preservative or other commonly used adjuvants.

In another aspect, the present disclosure provides a method for relieving skin itch or skin irritation, which includes administering an effective amount of a composition containing thymol trimethoxycinnamate or a stereoisomer, salt, hydrate or solvate thereof to a subject in need of relieving skin itch or skin irritation. In an aspect, the administration may be made according to the administration method and administration dosage described in the present disclosure.

In another aspect, the present disclosure provides a use of thymol trimethoxycinnamate or a stereoisomer, salt, hydrate or solvate thereof for preparation of a composition for relieving skin itch or skin irritation.

In another aspect, the present disclosure provides a use of thymol trimethoxycinnamate or a stereoisomer, salt, hydrate or solvate thereof for relieving skin itch or skin irritation.

Hereinafter, the present disclosure will be described in detail through examples, etc. However, the following examples are for illustrative purposes only and it will be obvious to those having ordinary skill in the art that the scope of the present disclosure is not limited by the examples.

[Example 1] Thymol Trimethoxycinnamate

Thymol trimethoxycinnamate (CAS No. 504394-57-4) was purchased from COSMANN Co., Ltd. (Hwaseong, Gyeonggi-do, Korea).

[Test Example 1] Evaluation of Effect of Inhibiting Voltage-Gated Sodium Channel Nav1.7

Human Nav1.7-HEK293 cells (Millipore) were used to evaluate the effect of inhibiting the voltage-gated sodium channel Nav1.7 of thymol trimethoxycinnamate. Human Nav1.7-HEK293 cells are HEK293 (human embryonic kidney 293) cells stabilized by transforming the human Nav1.7 gene. One day before experiment, the Human Nav1.7-HEK293 cells were dispensed onto a 96-well plate with $8 \times 10^4$ cells/well and cultured in a 5% $CO_2$ incubator at 37° C. for 24 hours. DMEM/F12 containing 10% fetal bovine serum (FBS) was used as a culture medium and geneticin (Gibco®, Thermo Fisher Scientific) was added to stabilize the cells.

24 hours later, after washing the 96-well plate once with a 20 mM HEPES Hanks' balanced salt solution (HBSS) buffer (hereinafter, referred to as a reaction buffer, Invitrogen®, Thermo Fisher Scientific), a membrane potential fluorescence dye (FLIPR®, Molecular Devices) was added to the human Nav1.7-HEK293 cells. After reaction in a 5% $CO_2$ incubator at 37° C. for about 40 minutes, the human Nav1.7-HEK293 cells were treated with the thymol trimethoxycinnamate of Example 1. After reaction for 10 minutes, the change in membrane potential depending on treatment with 30 μM veratridine as a stimulant was measured for each well for 55 seconds using a fluorescence plate reader (FlexStation3, Molecular Device, USA).

The change in the initial and maximum fluorescence intensities after treatment with Example 1, the reaction buffer only and veratridine for 55 seconds was determined. Then, inhibition rate was calculated by comparing the difference in values when veratridine was treated and only the reaction buffer was treated and the difference in values when Example 1 was treated and only the reaction buffer was treated. The inhibition rate was calculated in the same manner also for lidocaine (Sigma) which is used as a local anesthetic and itch-relieving agent. A result of comparing with Example 1 is shown in Table 1 and FIG. 1.

TABLE 1

|  | Example 1 | Lidocaine |
|---|---|---|
| $IC_{50}$ (μM) | 3.1 | 28.7 |

As a result, it was confirmed that the thymol trimethoxycinnamate of Example 1 alleviates skin itch and skin irritation in a concentration-dependent manner by inhibiting the voltage-gated sodium channel Nav1.7. In addition, it was confirmed that Example 1 has a superior effect of inhibiting the voltage-gated sodium channel Nav1.7 as compared to lidocaine of the same concentration.

[Test Example 2] Nav1.7 Human Sodium Ion Channel Cell-Based Automated Patch Clamp Assay Nav1.7 human sodium ion channel cell-based automated patch clamp assay (Eurofins, CYL8011QP2) was conducted. In a control step, the amplitude of current exceeding 200 pA was analyzed. The current amplitude was calculated by measuring the difference between the peak internal current and the residual current at the final step in −10 mV (current peak) steps. The current was evaluated under a vehicle control condition and then for 5 minutes after applying the compound.

The sodium channel is a) in resting or closed state at −120 mV, and b) in temporarily open deactivated state at 0 mV. The inhibition of channel opening (pulse 1) is measured from the sodium current at 0 mV within 1-2 ms. In order to completely deactivate the sodium channel and facilitate deactivated state-dependent drug biding, the channel was maintained longer in the open state (0 mV) and then returned to the deactivated resting or closed state at −120 mV for 10 ms. Then, the inhibition of the deactivated state (pulse 2) was evaluated at 0 mV for 50 ms. The compound was applied with each concentration for 5 minutes. The result is shown in Table 2.

TABLE 2

|  | Inhibition rate (%) | |
|---|---|---|
| Example 1 (μM) | Pulse 1 | Pulse 2 |
| 10 | 0.07 | 6.60 |
| 30 | 4.30 | 23.20 |
| 60 | 0.93 | 24.67 |
| 100 | 15.26 | 53.23 |
| 200 | 15.17 | 65.02 |

As can be seen from Table 2, the inhibitory effect depending on the concentration of Example 1 was confirmed for both pulse 1 and pulse 2.

[Test Example 3] Clinical Evaluation of Itch-Relieving Effect

Itch-relieving effect was evaluated on subjects suffering from chronic itch due to skin dryness, atopic dermatitis, sensitive skin, etc. When itch occurred for 30 minutes or longer, a lotion containing Example 1 at a concentration of 0.5% was applied and the degree of itch before and after the application was with a numerical rating scale. The degree of itch was evaluated with time at 2 minutes, 10 minutes and 30 minutes after the onset of itch from 0 (no itch) to 10 (worst itch imaginable) scores. The result is shown in FIG. 2 ( $p<0.01$, * $p<0.001$). The composition of the lotion containing Example 1 is shown in Table 3.

TABLE 3

| Ingredients | Contents (wt %) |
|---|---|
| Glyceryl stearyl citrate | 1.5 |
| $C_{12-15}$ alkyl benzoate and $C_{12-15}$ alcohol | 7.5 |
| Octyldodecanol | 3.0 |
| Cetearyl alcohol | 1.0 |
| Example 1 | 0.5 |
| Tromethamine | 0.1 |

TABLE 3-continued

| Ingredients | Contents (wt %) |
| --- | --- |
| Carbomer | 0.15 |
| Ethylhexylglycerin | 0.05 |
| Glyceryl caprylate | 0.1 |
| Hexanediol | 0.9 |
| Purified water | Balance |
| Total | 100.0 |

As shown in FIG. 2, it was found out that itch was inhibited significantly at all times after the application of a lotion containing Example 1.

[Formulation Example 1] Beauty Solution

A beauty solution was prepared according to a common method with a composition described in Table 4.

TABLE 4

| Ingredients | Contents (wt %) |
| --- | --- |
| Thymol trimethoxycinnamate | 0.1 |
| Glycerin | 3.0 |
| Butylene glycol | 2.0 |
| Propylene glycol | 2.0 |
| Carboxyvinyl polymer | 0.1 |
| PEG 12 nonyl phenyl ether | 0.2 |
| Polysorbate 80 | 0.4 |
| Ethanol | 10.0 |
| pH control agent | 0.1 |
| Antiseptic, pigment and flavor | 0.1 |
| Purified water | Balance |
| Total | 100 |

[Formulation Example 2] Cream

A cream was prepared according to a common method with a composition described in Table 5.

TABLE 5

| Ingredients | Contents (wt %) |
| --- | --- |
| Thymol trimethoxycinnamate | 1 |
| Polysorbate 80 | 1.5 |
| Sorbitan sesquioleate | 0.5 |
| PEG 60 hydrogenated castor oil | 2.0 |
| Liquid paraffin | 10.0 |
| Squalane | 5.0 |
| Caprylic/capric triglyceride | 5.0 |
| Glycerin | 5 |
| Butylene glycol | 3.0 |
| Propylene glycol | 3.0 |
| pH control agent | 0.2 |
| Antiseptic, pigment and flavor | 0.1 |
| Purified water | Balance |
| Total | 100 |

[Formulation Example 3] Lotion

A lotion was prepared according to a common method with a composition described in Table 6.

TABLE 6

| Ingredients | Contents (wt %) |
| --- | --- |
| Glyceryl stearyl citrate | 1.5 |
| $C_{12-15}$ alkyl benzoate and $C_{12-15}$ alcohol | 7.5 |
| Octyldodecanol | 3.0 |
| Cetearyl alcohol | 1.0 |
| Thymol trimethoxycinnamate | 0.5 |
| Tromethamine | 0.1 |
| Carbomer | 0.15 |
| Ethylhexylglycerin | 0.05 |
| Glyceryl caprylate | 0.1 |
| Hexanediol | 0.9 |
| Purified water | Balance |
| Total | 100.0 |

[Formulation Example 4] Massage Cream

A massage cream was prepared according to a common method with a composition described in Table 7.

TABLE 7

| Ingredients | Contents (wt %) |
| --- | --- |
| Thymol trimethoxycinnamate | 0.5 |
| Beeswax | 10.0 |
| Polysorbate 80 | 1.5 |
| PEG 60 hydrogenated castor oil | 2.0 |
| Sorbitan sesquioleate | 0.8 |
| Liquid paraffin | 40 |
| Squalane | 5.0 |
| Caprylic/capric triglyceride | 4.0 |
| Glycerin | 5.0 |
| Butylene glycol | 3.0 |
| Propylene glycol | 3.0 |
| pH control agent | 0.2 |
| Antiseptic, pigment and flavor | 0.1 |
| Purified water | Balance |
| Total | 100 |

[Formulation Example 5] Pack

A pack was prepared according to a common method with a composition described in Table 8.

TABLE 8

| Ingredients | Contents (wt %) |
| --- | --- |
| Thymol trimethoxycinnamate | 1 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG12 nonyl phenyl ether | 0.3 |
| Polysorbate 60 | 0.3 |
| Antiseptic, pigment and flavor | 0.1 |
| Purified water | Balance |
| Total | 100 |

[Formulation Example 6] Gel

A gel was prepared according to a common method with a composition described in Table 9.

TABLE 9

| Ingredients | Contents (wt %) |
| --- | --- |
| Thymol trimethoxycinnamate | 0.5 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG12 nonyl phenyl ether | 0.3 |
| Polysorbate 60 | 0.3 |
| Antiseptic, pigment and flavor | 0.1 |
| Purified water | Balance |
| Total | 100 |

[Formulation Example 7] Ointment

An ointment was prepared according to a common method with a composition described in Table 10.

TABLE 10

| Ingredients | Contents (wt %) |
| --- | --- |
| Thymol trimethoxycinnamate | 1.0 |
| Glycerin | 8.0 |
| Butylene glycol | 4.0 |
| Liquid paraffin | 15.0 |
| β-G | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and flavor | 0.1 |
| Purified water | Balance |
| Total | 100 |

[Formulation Example 8] Hair Lotion

A hair lotion was prepared according to a common method with a composition described in Table 11.

TABLE 11

| Ingredients | Contents (wt %) |
| --- | --- |
| Thymol trimethoxycinnamate | 1 |
| Liquid paraffin | 7.0 |
| Cetearyl glucoside | 1.5 |
| Sorbitan stearate | 0.4 |
| Squalane | 5.0 |
| Caprylic/capric triglyceride | 3.0 |
| Polysorbate | 1.2 |
| Carbomer | 0.1 |
| Glycerin | 3.0 |
| Butylene glycol | 3.0 |
| pH control agent | 0.2 |
| Antiseptic, pigment and flavor | 0.1 |
| Purified water | Balance |
| Total | 100 |

[Formulation Example 9] Soft Capsule

A soft capsule was prepared by mixing 100 mg of thymol trimethoxycinnamate, 160 mg of L-carnitine, 320 mg of soybean oil, 2 mg of palm oil, 8 mg of hydrogenated vegetable oil, 4 mg of yellow beeswax and 6 mg of lecithin and filling the mixture in a capsule according to a common method.

[Formulation Example 10] Tablet

A tablet was prepared by mixing 120 mg of thymol trimethoxycinnamate, 500 mg of galactooligosaccharide, 80 mg of lactose and 220 mg of maltose, granulating the mixture in a fluidized-bed dryer and then adding 6 mg of sugar ester.

[Formulation Example 11] Granule

A granule was prepared by mixing 100 mg of thymol trimethoxycinnamate, 250 mg of anhydrous crystalline glucose and 550 mg of starch, forming the mixture into a granule using a fluidized-bed granulator and then filling the granule in a pouch.

[Formulation Example 12] Drink

After mixing 120 mg of thymol trimethoxycinnamate, 10 g of glucose, 0.6 g of citric acid and 25 g of oligosaccharide syrup, 500 mL of purified water was added and 200 mL of the mixture was filled in a bottle. Then, a drink was prepared by sterilizing at 130° C. for 4-5 seconds.

The invention claimed is:

1. A method for relieving skin itch or skin irritation, comprising administering an effective amount of a composition comprising thymol trimethoxycinnamate or a stereoisomer, salt, hydrate or solvate thereof to a subject in need of relieving skin itch or skin irritation.

2. The method according to claim 1, wherein the thymol trimethoxycinnamate is represented by Chemical Formula 1:

[Chemical Formula 1]

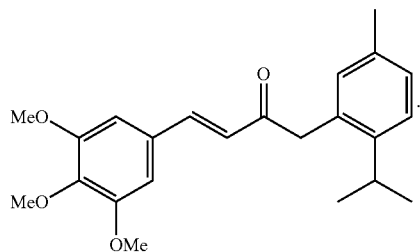

3. The method according to claim 1, wherein an administration dosage of the thymol trimethoxycinnamate or a stereoisomer, salt, hydrate or solvate thereof is 0.37-37 mg/kg/day.

4. The method according to claim 1, wherein a content of the thymol trimethoxycinnamate or a stereoisomer, salt, hydrate or solvate thereof is 0.001-20 wt % based on the total weight of the composition.

5. The method according to claim 1, wherein the relieving skin itch or skin irritation is by inhibiting the voltage-gated sodium channel Nav1.7.

6. The method according to claim 1, wherein the skin itch or skin irritation is induced by a chemical substance.

7. The method according to claim 1, wherein the composition is a composition for external application to skin.

8. The method according to claim 1, wherein the composition is a food composition.

9. The method according to claim 1, wherein the composition is a cosmetic composition.

10. The method according to claim 1, wherein the composition is a pharmaceutical composition.

* * * * *

UNITED STATES PATENT AND TRADEMARK OFFICE
CERTIFICATE OF CORRECTION

PATENT NO. : 11,583,512 B2  
APPLICATION NO. : 17/388581  
DATED : February 21, 2023  
INVENTOR(S) : Yeonsu Jeong and Bongsoo Pi Page 1 of 1

It is certified that error appears in the above-identified patent and that said Letters Patent is hereby corrected as shown below:

In the Specification

Column 2, Lines 20-31, delete " 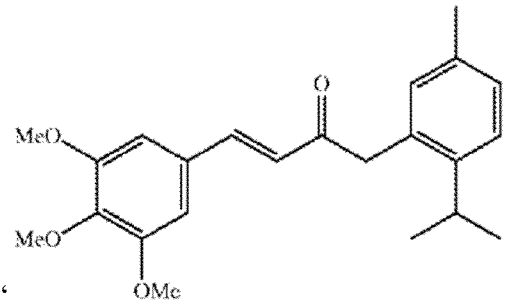 " and insert -- 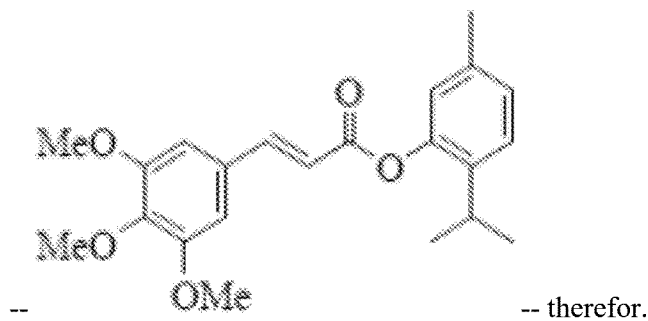 -- therefor.

Signed and Sealed this  
Fourth Day of April, 2023

Katherine Kelly Vidal  
*Director of the United States Patent and Trademark Office*